US008894602B2

(12) United States Patent
Coldren (10) Patent No.: US 8,894,602 B2
(45) Date of Patent: Nov. 25, 2014

(54) PUNCTAL PLUGS WITH DIRECTIONAL RELEASE (75) Inventor: Bret A. Coldren, Vista, CA (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/196,282

(22) Filed: Aug. 2, 2011

(65) Prior Publication Data

US 2012/0197217 A1    Aug. 2, 2012

Related U.S. Application Data (60) Provisional application No. 61/383,897, filed on Sep. 17, 2010.

(51) Int. Cl.
A61B 19/00 (2006.01)
A61M 35/00 (2006.01)
A61F 9/007 (2006.01)
A61F 9/00 (2006.01)

(52) U.S. Cl.
CPC ........... A61F 9/00772 (2013.01); A61F 9/0017 (2013.01)
USPC ............. 604/8; 604/294; 604/891.1; 128/898

(58) Field of Classification Search
CPC ..... A61F 9/00781; A61B 19/00; A61M 35/00
USPC .............................. 604/8, 294, 891.1; 128/898
See application file for complete search history.

(56) References Cited

U.S. PATENT DOCUMENTS

| 3,618,604 | A |   | 11/1971 | Ness |
| 3,626,940 | A |   | 12/1971 | Zaffaroni |
| 3,826,258 | A |   | 7/1974  | Abraham |
| 3,845,770 | A |   | 11/1974 | Theeuwes et al. |
| 3,949,750 | A |   | 4/1976  | Freeman |
| 3,962,414 | A |   | 6/1976  | Michaels |
| 3,993,071 | A |   | 11/1976 | Higuchi et al. |
| 4,014,335 | A |   | 3/1977  | Arnold |
| 4,923,699 | A |   | 5/1990  | Kaufman |
| 5,868,697 | A | * | 2/1999  | Richter et al. ............ 604/8 |
| 5,962,548 | A |   | 10/1999 | Vanderlaan et al. |
| 6,020,445 | A |   | 2/2000  | Vanderlaan et al. |
| 6,099,852 | A |   | 8/2000  | Jen |
| 6,149,684 | A | * | 11/2000 | Herrick ............... 623/4.1 |

(Continued)

FOREIGN PATENT DOCUMENTS

WO    WO 2006/096586 A1    9/2006
WO    WO 2007/149773 A2    12/2007

OTHER PUBLICATIONS

U.S. Appl. No. 13/043,171, Nathan R.F. Beeley, et al., Mar. 8, 2011.

Primary Examiner — Tatyana Zalukaeva
Assistant Examiner — Sara Sass
(74) Attorney, Agent, or Firm — Carl J. Evens (57) ABSTRACT Disclosed are lacrimal inserts and their method of use for delivery of medication to the eye. The plug includes a body portion sized to pass through a lacrimal punctum and be positioned within a lacrimal canaliculus of the eyelid and includes means for directional release of medication into the lacrimal fluid. The plug may contain a core, or reservoir, at least partially within the body portion comprising a therapeutic agent that is configured to controlled release into the eye.

1 Claim, 6 Drawing Sheets

(56) References Cited

U.S. PATENT DOCUMENTS

| | | |
|---|---|---|
| 6,196,993 B1 | 3/2001 | Cohan et al. |
| 6,367,929 B1 | 4/2002 | Maiden et al. |
| 6,822,016 B2 | 11/2004 | McCabe et al. |
| 6,994,684 B2 * | 2/2006 | Murray et al. .................. 604/8 |
| 2004/0127843 A1 * | 7/2004 | Tu et al. ......................... 604/27 |
| 2006/0020248 A1 | 1/2006 | Prescott |
| 2006/0020253 A1 * | 1/2006 | Prescott ....................... 604/500 |
| 2009/0306608 A1 | 12/2009 | Li et al. |

* cited by examiner

PUNCTAL PLUGS WITH DIRECTIONAL RELEASE

CROSS REFERENCE TO RELATED APPLICATIONS

This patent application claims the benefit of U.S. Provisional Patent Application Ser. No. 61/383,897 filed Sep. 17, 2010.

BACKGROUND OF THE INVENTION

1. Field of the Invention

The present invention relates to an ophthalmic insert and method for the release of medication to the eye for the treatment of eye disorders. More specifically, the present invention relates to punctal plugs sized to pass through a lacrimal punctum and be positioned within a lacrimal canaliculus of the eyelid and containing medication for controlled, directional release into the eye in a therapeutically effective amount in a pulsatile or continuous manner, or combinations thereof.

2. Discussion of the Related Art

Active agents frequently are administered to the eye for the treatment of ocular diseases and disorders. Conventional means for delivering active agents to the eye involve topical application to the surface of the eye. The eye is uniquely suited to topical administration because, when properly constituted, topically applied active agents can penetrate through the cornea and rise to therapeutic concentration levels inside the eye. Active agents for ocular diseases and disorders may be administered orally or by injection, but such administration routes are disadvantageous in that, in oral administration, the active agent may reach the eye in too low a concentration to have the desired pharmacological effect and their use is complicated by significant, systemic side effects and injections pose the risk of infection.

The majority of ocular active agents are currently delivered topically using eye drops which, though effective for some applications, are inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Therefore, sometimes one or more drops miss the eye. Older patients may have additional problems instilling drops due to arthritis, unsteadiness, and decreased vision, and pediatric and psychiatric patient populations pose difficulties as well.

It is known to use devices that may be inserted into one or more of an orifice of an individual's eye, such as a lacrimal punctum, to deliver active agents. One disadvantage of using such devices to deliver agents is that much of the agent may delivered in an initial, large bolus upon insertion of the device into the eye rather than a more linear delivery of the agent over time.

Prior topical sustained release systems include gradual release formulations, either in solution or ointment form, which are applied to the eye in the same manner as eye drops but less frequently. Such formulations are disclosed, for example, in U.S. Pat. No. 3,826,258 issued to Abraham and U.S. Pat. No. 4,923,699 issued to Kaufman. Due to their method of application, however, these formulations result in many of the same problems detailed above for conventional eye drops. In the case of ointment preparations, additional problems are encountered such as a blurring effect on vision and the discomfort of the sticky sensation caused by the thick ointment base.

Alternately, sustained release systems have been configured to be placed into the conjunctival cul-de-sac, between the lower lid and the eye. Such units typically contain a core drug-containing reservoir surrounded by a hydrophobic copolymer membrane which controls the diffusion of the drug. Examples of such devices are disclosed in U.S. Pat. No. 3,618,604 issued to Ness, U.S. Pat. No. 3,626,940 issued to Zaffaroni, U.S. Pat. No. 3,845,770 issued to Theeuwes et al., U.S. Pat. No. 3,962,414 issued to Michaels, U.S. Pat. No. 3,993,071 issued to Higuchi et al., and U.S. Pat. No. 4,014,335 issued to Arnold. However, due to their positioning, the units are uncomfortable and poor patient acceptance is again encountered.

It would, therefore, be desirable to provide a punctal insert that overcomes the shortcomings of prior art devices and can facilitate more precise delivery of medication to the lacrimal fluid.

SUMMARY OF THE INVENTION

The punctual plug or insert containing a drug formulation of the present invention overcomes many of the disadvantages associated with the prior art.

In accordance with one aspect, the present invention is directed to a lacrimal insert. The lacrimal insert comprising a body having a first end and a second end; a surface extending between the two ends, a reservoir contained within the body, wherein the reservoir comprises at least one opening, an active agent-containing material and an active agent; a channel within the first end or the second end in fluid communication with the reservoir; and a means to release the contents of the reservoir through the channel in a direction towards the ocular surface.

The present invention is directed to punctual plugs sized to pass through a lacrimal punctum and be positioned within a lacrimal canaliculis of the eyelid and which comprises one or more therapeutic agents for controlled release into the eye. The punctual plug is configured for easy insertion and long term stability. The plug is configured to hold the one or more therapeutic agents and release these one or more agents into the eye for treatment of a particular condition of the eye. The plug also comprises a channel which is in fluid communication with a reservoir that holds the one or more therapeutic agents that directs the one or more therapeutic agents to the proper location within the eye.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Punctal plugs have been in use for decades now to treat conditions of dry eye. More recently they have gained attention for use as drug delivery systems for the treatment of ocular diseases and conditions. Several challenges exist with formulating a drug to release at the desired daily rate and/or dose that is efficacious while limiting adverse events.

Diffusion based drug delivery systems are characterized by the release rate of a drug. This is dependent on its diffusion through an inert water insoluble membrane barrier. There are basically two diffusion designs; namely, reservoir devices and matrix devices. Reservoir devices are those in which a core of drug is surrounded by a polymeric membrane. The nature of the membrane determines the rate of release of a drug from system. The process of diffusion is generally described by a series of equations governed by Fick's first law of diffusion. A matrix device consists of drug dispersed homogenously throughout a polymer structure.

Reservoir and matrix drug delivery systems are considered diffusion based sustained release systems and constitute any dosage form that provides medication over an extended period of time. The goal of a sustained release system is to maintain therapeutic levels of drug for an extended period and this is usually accomplished by attempting to obtain zero-order release from the sustained release system. Sustained release systems generally do not attain this type of release profile but try to approximate it by releasing the drug in a slow first order manner. Over an extended period of time, the drug release rate from reservoir and matrix sustained release systems will decay and become non therapeutic.

Zero-order drug release constitutes drug release from a drug delivery system at a steady sustained drug release rate, that is, the amount of drug that is released from the drug delivery system over equal time intervals does not decay and remains at the therapeutic level. This "steady sustained release drug delivery system" is referred to as a zero-order drug delivery system and has the potential to provide actual therapeutic control by its controlled release.

Another drug release profile is referred to as pulsatile drug delivery. Pulsatile drug delivery is intended to release a therapeutic amount of a therapeutic agent at regular intervals. With any type of release profile (or combinations thereof), it has been found that the directional release of medication may provide improved performance of the lacrimal insert.

In general terms, three key factors are believed to contribute to inconsistent diffusive drug delivery to the human eye from a passive matrix lacrimal drug delivery device. First, the drug release matrix surface in contact with patient tear film becomes fouled to differing degrees by absorbed tear film components (lipids, proteins, cellular debris, etc) which inhibits diffusion of drug away from the matrix surface. Second, there are differing degrees of hydration, or tear volume, between patients. Individual patients of lower tear film volume can create varying dissolution limiting situations. Smaller local regions of drug saturation limit the rate of diffusion away from the drug delivery surface and hence the overall rate of drug release. And third, critical variations in the human anatomical positioning of the lacrimal punctum, and device inserted therein, relative to the ocular surface. In rabbits and dogs, the punctum is positioned deeper on the interior surface of the eyelid, in direct opposition to the tear film and bulbar conjunctiva, thereby, assuring optimal diffusive contact with the drug release surface regardless of minor variations in animal anatomy or device placement. In humans the punctum is located at the apex of the eye-lid margin, where sub-millimeter variations in human anatomy and/or punctum device placement may lead to drug release surfaces with significant variation in the quality of diffusive contact to a tear film of significantly varying volume. All three factors may be mitigated by a novel lacrimal device comprising the features set forth herein.

Specifically, an element or feature may be desirable to facilitate directional indexing of the lacrimal insert relative to the ocular surface of a human, such as a discernible mark, indentation, color, texture, shape, and the like. Further, the device may include a drug dispensing channel, pore, or valve structure that extends over, and/or is integrated into, some portion of a flange (positioned at the punctum opening) of the lacrimal drug delivery device. The dispensing channel, when positioned properly in a human subject, is directed towards the ocular surface. The dispensing channel is substantially impermeable to drug in its transverse direction, such that drug release is directed primarily along its axis and towards the ocular surface. The channel dimensions may be from 2 to 400 microns wide by 2 to 200 microns tall by at least 100 microns but not more than 5000 microns long, preferably not more than 1000 microns long.

A mechanism for drug release from the drug core of the lacrimal device is to be primarily active and convective and directed through the drug dispensing channel in a continuous or intermittent/pulsatile manner or any combination thereof. Alternately, the device may employ a passive-diffusive release from a rate-controlling matrix containing dispersed drug.

The flange region adjacent to, or incorporating the drug dispensing channel may comprise an extended shape and downward curvature (as shown illustratively in at least FIGS. 2-5) optimized for comfort and physical coupling to the tear film.

Figure 1:
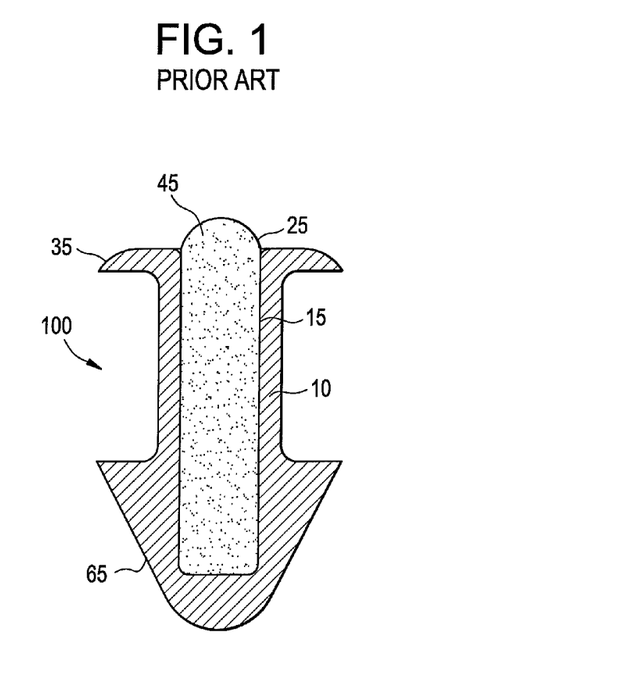
FIG. 1 illustrates a cross-sectional view of a typical lacrimal insert according to the prior art that does not employ means for directional release of a therapeutic agent.
Figure 2A:
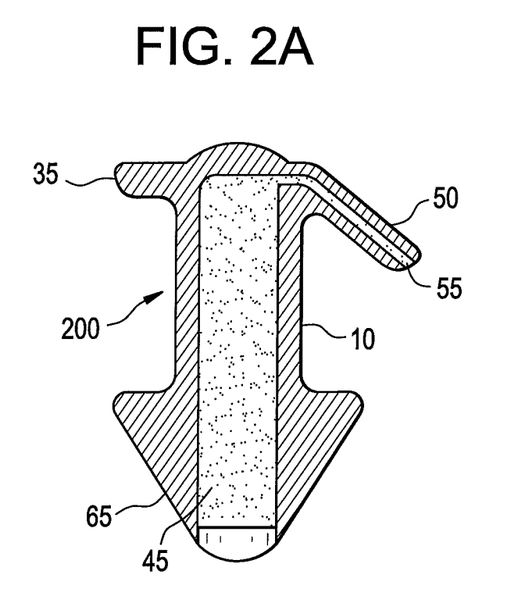
FIG. 2A shows an illustrative embodiment of the present invention wherein a lacrimal insert, shown in cross-section, comprises a structure that permits directional release of medication.
Figure 2B:
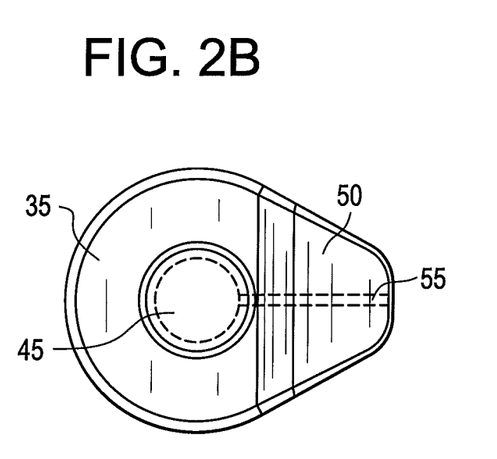
FIG. 2B shows the illustrative embodiment of FIG. 2A in top plan view.
Figure 3A:
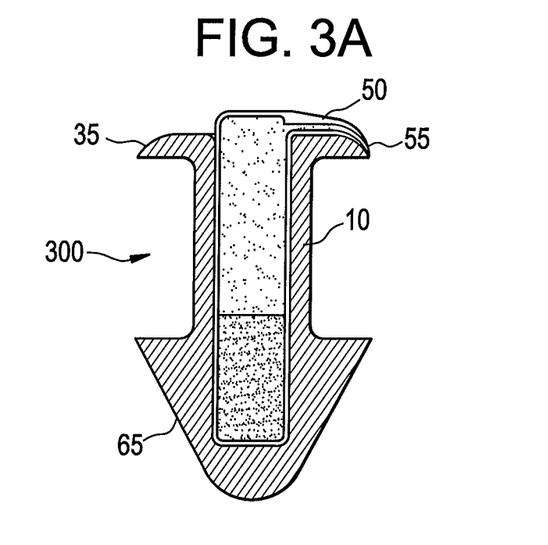
FIG. 3A shows another illustrative embodiment of the present invention wherein a lacrimal insert, shown in cross-section, comprises a structure that permits directional release of medication.
Figure 3B:
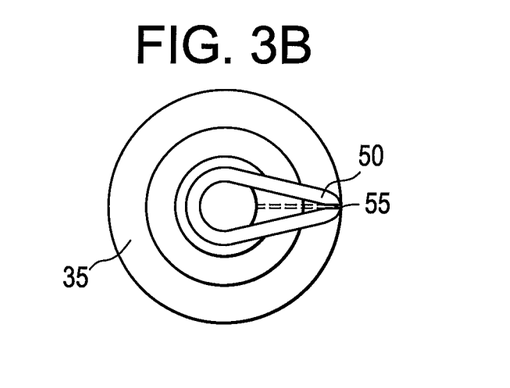
FIG. 3B shows the illustrative embodiment of FIG. 3A in top plan view.
Figure 4A:
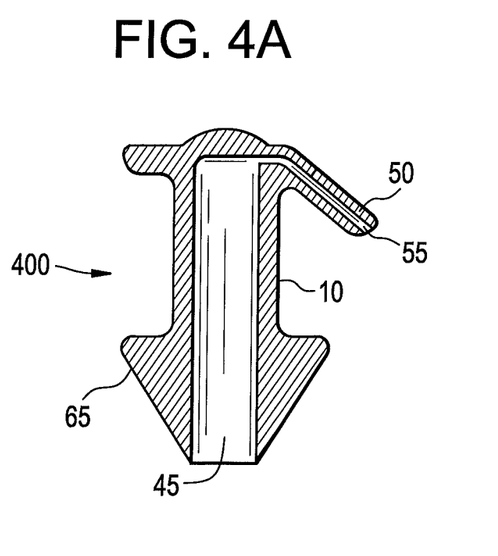
FIG. 4A show another exemplary embodiment of the present invention in which a lacrimal insert comprises a structure to permit directional release of medication.
Figure 4B:
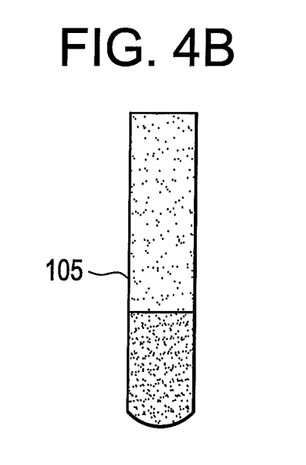
FIG. 4B shows a pre-assembled drug-core insert for use in a lacrimal insert, in cross-section in accordance with the present invention.
Figure 4C:
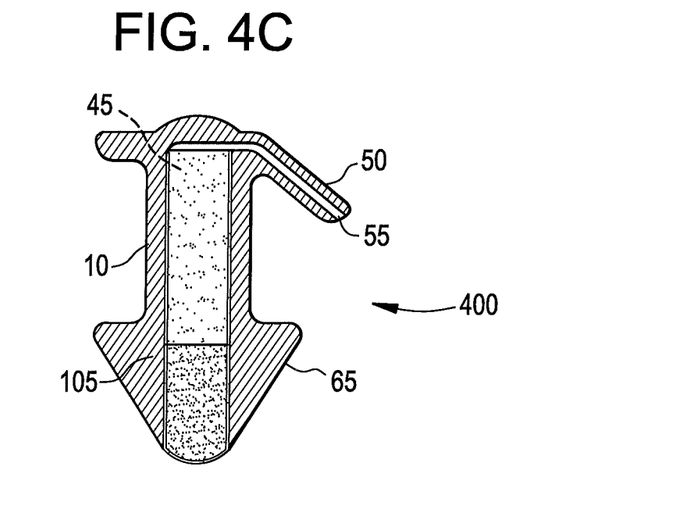
FIG. 4C shows the lacrimal insert of FIG. 4A with the drug-core insert of FIG. 4B inserted therein.
Figure 5A:
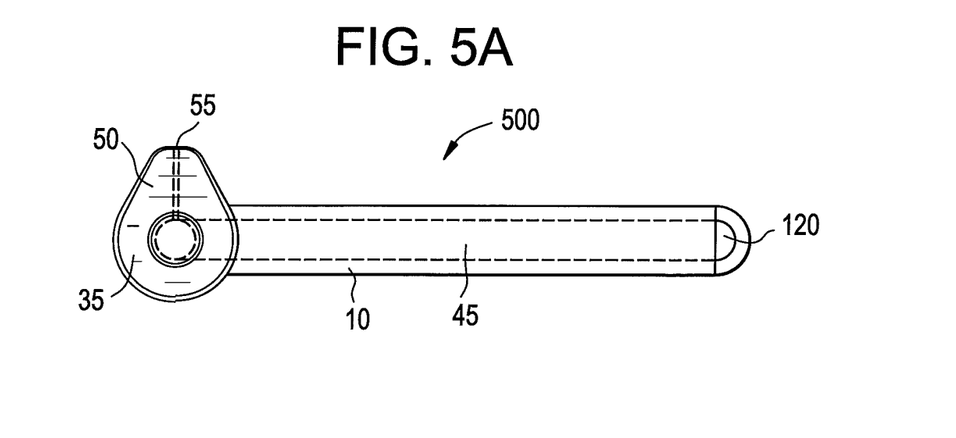
FIG. 5A shows another exemplary embodiment of a lacrimal inert with directional release capability having an elongated housing to permit directional insertion in a lacrimal canaliculus in accordance with the present invention.
Figure 5B:
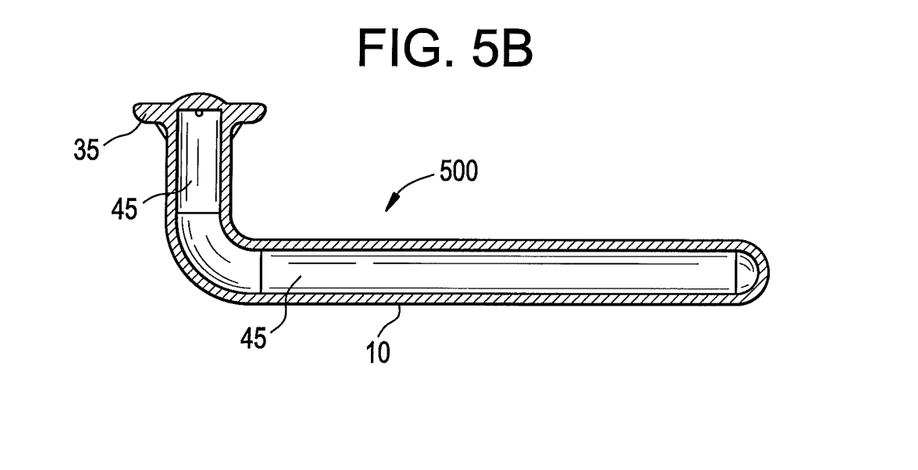
FIG. 5B shows a side view of the embodiment of FIG. 5A.
Figure 5C:
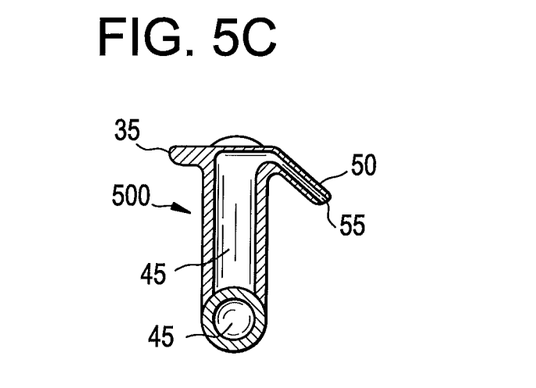
FIG. 5C shows an end view of the exemplary embodiment of FIG. 5B.

The body enclosing the drug core component of the lacrimal device may resemble a conventional Freeman-style, as illustrated in U.S. Pat. No. 3,949,750, which is hereby incorporated by reference in its entirety. Thus, a device according to an exemplary embodiment of the present invention may generally have the form of a punctal plug with a proximal flange connected to a hollow cylindrical body and distal arrow-head-like retention structure, as shown in FIGS. 2-4. The body may alternately resemble a canalicular stent, wherein the proximal flange is attached to a tubular body structure that extends distally past the human punctum and into the horizontal canaliculus or even as far as the lacrimal sac, as illustrated in FIG. 5.

The drug core component may comprise a variety of reservoir-pump configurations known in the art of drug delivery to achieve active displacement of a liquid or semisolid drug formulation. Such mechanisms may comprise water penetration, with expansion of a hydrogel and/or osmotic-based engine. Mechanisms with water penetration into the device may also lead to gas-generation and positive displacement, via a chemical or electrochemical reaction. Mechanisms may also comprise a microelectromechanical system (MEMS) with positive displacement pumping of drug formulation. Osmotic, hydrogel, gas-generating, and MEMS-based fluid displacement technologies are known and enabled in the art.

The drug core component may comprise an outer shell or sleeve structure that serves a mechanical/structural function as well as a water and/or drug diffusivity barrier.

Flowable liquid or semisolid formulations are necessary for flow through a channel, versus solid drug formulations. In some exemplary embodiments viscous liquid or semisolid formulations are desirable for their resistance to creep or gravitational flow and leakage from the device, and particularly a greater ease of handling and manufacturing and assembly of sub-components, relative to low viscosity liquid formulations (<100 centipoise). Neat viscous oils are formed by multiple prostaglandin drugs, for example, latanoprost and travaprost. Simple pharmaceutically-acceptable solubilizing additives may be blended with bimatoprost powder to achieve similar viscous oil formulations.

Active displacement of liquid or semisolid formulations through a dispensing channel with substantially sub-millimeter dimensions necessitates consideration of the relationship between the desired range of output flow rates and the driving pressure, formulation viscosity, and dispensing channel dimensions. Utilizing the Hagen-Poiseuille equation to predict flowrates of a Newtonian fluid in a tubular channel under incompressible laminar flow conditions is set forth in the example below.

EXAMPLE

Driving pressure: 1 psi
Formulation viscosity: 1500 centipoise
Formulation density: 1.5 gm/cc

| Tubular Channel Dims (dia × L, microns) | Formulation flowrate (nL/hr) |
|---|---|
| 9 × 100 | 26.6 |
| 10 × 100 | 40.6 |
| 11 × 100 | 59.5 |
| 10 × 400 | 10.15 |
| 10 × 1000 | 4.06 |
| 50 × 100 | 25000 |
| 50 × 400 | 6000 |
| 50 × 1000 | 2500 |
| 100 × 100 | 406000 |
| 100 × 1000 | 40600 |

Demands on flowrate through the dispensing channel are greatest for pulsatile drug release modes of device operation. In the specific case of pulsatile delivery of a prostaglandin for glaucoma, a desirable pulsed delivery bolus could equate to about 25 nanoliters per hour. In this case, channel diameters below 10 microns and/or longer than 400 microns may become undesirable for formulations of viscosity>1000 cP.

Channels of diameter larger than 100 microns and shorter than 100 microns in length may lead to undesirable parasitic diffusion of drug out of the device between intended pulses, as well as undesirable ingress of external tear film components (water, salts, proteins, lipids, cellular and noncellular debris, and the like).

A device according to the present invention may, in one exemplary embodiment, have structure as generally shown in FIGS. 2-5 wherein a lacrimal insert 200,300,400,500 includes an elongated housing 10, a first end 65 that may be tapered to pass through the lacrimal punctum, and a second end 35 with a flange for resting on the ocular surface adjacent to the lacrimal punctum. The second end 35 may include directional release feature 50 that has a channel, pore, or other feature 55 that is in fluid communication with a reservoir 45. When a drug core, such as the drug core 105 shown in FIGS. 4A and 4B, is inserted into the reservoir 45, the therapeutic agent or active-agent containing material may be release via the channel 55 into the lacrimal fluid.

Figure 6:
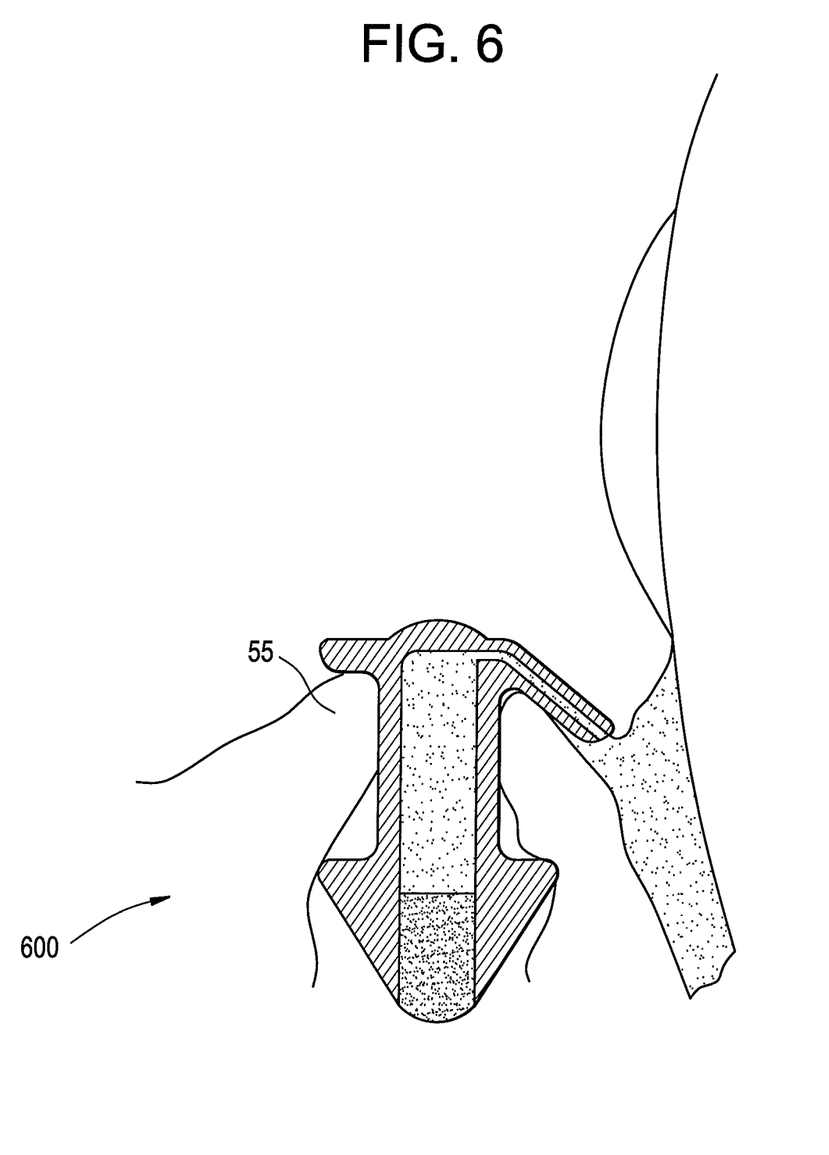
FIG. 6 shows the lacrimal insert of the present invention in place on the eye.

The entire plug 200,300,400 may be rotated within the punctum to direct the release of medication from the channel 55 in the direction of the ocular surface. With an embodiment similar to the punctal plug 500 illustrated in FIG. 5A, the elongated portion of the housing, or canalicular extension, may be oriented to point in the direction of the nasal cavity to ensure release of the drug or therapeutic agent in directional alignment with the ocular surface. Referring to FIG. 6, the lacrimal insert 600 is placed into the canaliculus of the eye, and oriented such that the medication is released from the channel 55 in a direction towards the globe of the eye.

Human clinical delivery of a drug from a punctal plug having a passive diffusion matrix mechanism with a concentric geometrical pattern results in highly inconsistent amounts of delivered drug from patient to patient, compared to similar studies performed in rabbit, dog, or in-vitro. While not wishing to be bound by theory, it has been suggested that there are three main factors that contribute to the poor human clinical performance of passive diffusion from the flange-centered core of a conventional Freeman-style plug.

First, the drug release matrix surface in contact with patient tear film becomes fouled to differing degrees by absorbed tear film components (lipids, proteins, cellular debris, and the like) which inhibits diffusion of drug away from the matrix surface. Second, the differing degrees of hydration, or tear volume, between patients. Individual patients of lower tear film volume can create varying dissolution limiting situations. Smaller local regions of drug saturation limit the rate of diffusion away from the drug delivery surface and hence the overall rate of drug release. And third, critical variations in the human anatomical positioning of the lacrimal punctum, and device inserted therein, relative to the ocular surface. In rabbits and dogs, the punctum is positioned deeper on the interior surface of the eyelid, in direct opposition to the tear film and bulbar conjunctiva—assuring optimal diffusive contact with the drug release surface regardless of minor variations in animal anatomy or device placement. In humans the punctum is located at the apex of the eye-lid margin, where sub-millimeter variations in human anatomy and/or punctum device placement can lead to drug release surfaces with significant variation in the quality of diffusive contact to a tear film of significantly varying volume.

As used herein, the term "active agent" refers to an agent capable of treating, inhibiting, or preventing a disorder or a disease. Exemplary active agents include pharmaceuticals and nutraceuticals. Preferred active agents are capable of treating, inhibiting, or preventing a disorder or a disease of one or more of the eye, nose and throat.

As used herein, the term "punctal plug" refers to a device of a size and shape suitable for insertion into the inferior or superior lacrimal canaliculus of the eye through, respectively, the inferior or superior lacrimal punctum. Exemplary and illustrative devices are disclosed in U.S. Pat. No. 6,196,993 and U.S. Published Patent Application No. 20090306608A1, both of which are hereby incorporated by reference in their entireties. Examples of punctual plugs with osmotically controlled drug delivery systems are also described in commonly owned, copending U.S. Application Ser. No. Ser. No. 61/322,127, filed on Apr. 8, 2010, which is hereby incorporated by reference in its entirety.

As used herein, the term "opening" refers to an opening in the body of a device of the invention of a size and shape through which the active agent can pass. Preferably, only the active agent and formulation can pass through the opening. The opening may be covered with a membrane, single or multiple pores, mesh, grid or it may be uncovered. The membrane, mesh, or grid may be one or more of porous, semiporous, permeable, semi-permeable, and biodegradable.

The devices of the present invention have a reservoir in which is found an active agent-containing material and an active agent therein. The active agent may be dispersed throughout the active agent-containing material or dissolved within the material. Alternately, the active agent may be contained in inclusions, particulates, droplets, beads, or microencapsulated within the material. Still as another alternate, the active agent may be covalently bonded to the material and released by hydrolysis, enzymatic degradation and the like. Yet as another alternate, the active agent may be in a reservoir within the material.

It is a discovery of the present invention that the active agent may be released in a controlled manner, meaning over a period of time by using an active agent-containing material in which the agent is present in a substantially continuous concentration gradient throughout the material or by using a discontinuous concentration gradient. This is in contrast to a device that exhibits a "burst" or immediate release upon insertion of an amount of active agent that is greater than the average release rate over time.

The local gradient may be controlled by placing more active agent at one location in the active agent-containing material relative to another location. For example, the concentration profile may be a continuous gradient from one end of the material to the other. Alternately, the matrix may have a discontinuous gradient, meaning that one section of the material has a first concentration and the concentration abruptly changes to a second, different concentration in an adjacent section of the matrix. The diffusivity for the active agent may also be spatially controlled by varying one or more of the chemical composition, porosity, and crystallinity of the active agent-containing material.

Additionally, the spatial variation of the material's cross-sectional geometry may be used to control diffusivity. For example, if the material was in the form of a straight rod that has a uniform active agent concentration, diffusivity will be reduced when the area at the open end of the material is significantly smaller than the average of the entire material. Preferably, the material area at the open end of the device is no more than one-half of the average cross sectional area of the material, meaning that the cross section determined perpendicular to the primary dimension of active agent transport.

One of ordinary skill in the art will recognize that, depending on how one varies one or more of the local concentration gradients, the diffusivity of the active agent from the material, and the spatial variation of the cross-sectional geometry of the device, a variety of release profiles may be obtained including, without limitation first order, second order, biphasic, pulsatile and the like. For example, either or both of the active agent concentration and diffusivity may increase from the surface to the center of the active agent-containing material in order to achieve more initial release. Alternately, either or both may be increased or decreased and then increased again within the material to achieve a pulsatile release profile. The ability to achieve a variety of release profiles by varying local concentration gradient, the diffusivity of the active agent, and the spatial variation of the cross-sectional geometry may eliminate the need for rate-limiting membranes in the device.

Alternately, it is a discovery of the present invention that small "bursts" of active-agent containing material may produce therapeutically effective dosing of active-agent into the desired treatment region. Such bursts may be accomplished by the periodic introduction of encapsulated active agent, as might be found in microcapsules, microbeads, and the like, or by creating a reservoir of active-agent containing material that delivers a period bolus of therapeutic material (i.e., active agent) by mechanical, electrical, chemical, or other means that are determined by the structure and geometry of a reservoir within the lacrimal insert.

Suitable polymeric materials for the active agent-containing material include hydrophobic and hydrophilic absorbable and non-absorbable polymers. Suitable hydrophobic, non-absorbable polymers include ethylene vinyl alcohol ("EVA"), fluorinated polymers including without limitation, polytetrafluoroethylene ("PTFE") and polyvinylidene fluoride ("PVDF"), polypropylene, polyethylene, polyisobutylene, nylon, polyurethanes, polyacrylates and methacrylates, polyvinyl palmitate, polyvinyl stearates, polyvinyl myristate, cyanoacrylates, epoxies, silicones, copolymers thereof with hydrophobic or hydrophilic monomers, and blends thereof with hydrophilic or hydrophobic polymers and excipients.

Hydrophilic, non-absorbable polymers useful in the present invention include cross-linked poly(ethylene glycol), poly(ethylene oxide), poly(propylene glycol), poly(vinyl alcohol), poly(hydroxyethyl acrylate or methacrylate), poly(vinylpyrrolidone), polyacrylic acid, poly(ethyloxazoline), and poly(dimethyl acrylamide), copolymers thereof with hydrophobic or hydrophilic monomers, and blends thereof with hydrophilic or hydrophobic polymers and excipients.

Hydrophobic, absorbable polymers that may be used in the present invention include aliphatic polyesters, polyesters derived from fatty acids, poly(amino acids), poly(ether-esters), poly(ester amides), polyalkylene oxalates, polyamides, poly(iminocarbonates), polycarbonates, polyorthoesteres, polyoxaesters, polyamidoesters, polyoxaesters containing amine groups, phosphoesters, poly)anhydrides), polypropylene fumarates, polyphosphazenes, and blends thereof. Examples of useful hydrophilic, absorbable polymers include polysaccharides and carbohydrates including crosslinked alginate, hyaluronic acid, dextran, pectin, hydroxyethyl cellulose, hydroxy propyl cellulose, gellan gum, guar gum, keratin sulfate, chondroitin sulfate, dermatan sulfate, proteins including collagen, gelatin, fibrin, albumin and ovalbumin, and phospholipids including phosphoryl choline derivatives and polysulfobetains.

More preferably, the active agent-containing material is a polymeric material that is polycaprolactone. Still more preferably, the material is poly(epsilon-caprolactone), and ethylene vinyl acetate of molecular weights between about 10,000 and 80,0000. About 0 to about 100 weight percent polycaprolactone and about 100 to about 0 weight percent of the ethylene vinyl acetate are used based on the total weight of the polymeric material and, preferably, about 50% each of polycaprolactone and ethylene vinyl acetate is used.

The polymeric material used is preferably greater than about 99% pure and the active agents are preferably greater than about 97% pure. One of ordinary skill in the art will recognize that in compounding, the conditions under which compounding is carried out will need to take into account the characteristics of the active agent to ensure that the active agents do not become degraded by the process. The polycaprolactone and ethylene vinyl acetate preferably are combined with the desired active agent or agents, micro-compounded, and then extruded.

In addition to or instead of active agent loading profiles, the release kinetics may be controlled via spatial gradients of the properties of degradability and drug permeability of the active agent-containing material. For example, in those cases in which drug release kinetics are dominated by the rate of material degradation, a spatial degradation in the material chemistry including polylactide-glycolide copolymers of differing monomer ratios, adjacent polyglycolide and polycaprolactone layers and the like, results in spatial gradients and varied release rates as the material degradation front moves through the device. By way of further example, a material may erode more slowly initially in a first, outer material and more quickly in a second, inner material to achieve phased release kinetics.

In the case of a non-degradable material that elutes the active agent solely through diffusion-dominated mechanisms, spatial gradients in the material's permeability may control release kinetics beyond what is possible with a homogeneous material. In the diffusion-dominated mechanism, the material permeability controls release kinetics and is influenced by the material's porosity as well as the active agent solubility and diffusivity. By forming an active agent-loaded layer of an outer material with a higher permeability, the active agent elution may be controlled to be more linear with less burst effect than that which is otherwise achieved with a single, homogeneous, diffusion material.

The spatial gradients in biodegradability or permeability may be combined with continuous or step-wise gradients in the active agent loading profile. For example, a punctal plug material core having an outer segment loaded with a low active agent concentration and with a relatively low active agent permeability may be adjacent to an inner material segment loaded with a high agent concentration and with a relatively high active agent permeability, which combination achieves release kinetics unobtainable with a homogeneous material ad homogeneous active agent loading. The initial burst release is reduced and the release of the last active agent content is accelerated relative to a conventional homogeneous active agent loaded device.

Phase-separated inclusions may be used to control one or both of diffusive and degradative kinetics of the active agent-containing material. For example, water soluble polymers, water soluble salts, materials with a high diffusivity for the active agent and the like may be used as destabilizing inclusion to enhance degradation or diffusion rates. When the hydrolysis front reaches an inclusion, the inclusion rapidly dissolves and increases porosity of the active agent-containing material. The inclusions may be incorporated as gradients or layers that allow additional tailoring of the release profile.

As another alternate, a percolated network of destabilizing inclusions may be used. When used in a non-biodegradable active agent-containing material, these inclusions form islands within the material that may possess high diffusivity for the active agent. Useful inclusions will have a higher diffusivity for the active agent than the active agent-containing material. Examples of such inclusions include propylene glycol, silicone oil, immiscible dispersed solids such as a polymer or wax and the like. As yet another example, an inclusion that acts to adsorb water, swell the active agent-containing material and increase local diffusion kinetics may be used.

As still another alternate, stabilizing inclusions that have a low active agent diffusivity are used. These inclusions act to form a barrier that slows diffusive transport of the active agent in the vicinity of the inclusion. The overall effect is a reduction of active agent permeability in a base material that is otherwise the same. Example of such inclusions include micro to nano-sized silicate particles dispersed through the base material of one or both of polycaprolactone and ethylenecovinylacetate homogeneously or in continuous step-wise gradients.

The present invention encompasses numerous devices for the delivery of active agents to the eye each having various features and advantages. For example, certain devices may have a body with a first end, a second end, and a lateral surface extending between the two ends. The lateral surface preferably has an outer diameter that is substantially circular in shape and, thus, the body preferably has a cylindrical shape. A portion of the lateral surface of certain of the devices preferably has an outer diameter that is greater than the outer diameter of the remainder of the lateral surface. The enlarged portion may be any size or shape, and may be present on any part of the lateral surface, in punctal plug embodiments, the enlarged portion is of a size so that it at least partially anchors the punctal plug in the lacrimal canaliculus and preferably, the enlarged portion is at one end of the plug. One ordinarily skilled in the art will recognize that any of a wide variety of shapes are possible.

The body of the punctal plugs of the invention may take any shape and size, preferably, the body is in the shape of an elongated cylinder, e.g. tubular. The body may be from about 0.5 to about 10 mm in length. The width of the body may be from about 0.2 to about 3, preferably 0.3 to about 1.5 mm, although those skilled in the art will recognize that the sizing of the device may be wholly dependent on the size of the lacrimal puncta of the patient. Thus, larger or smaller size than those specifically recited herein may be needed in situations where the device is intended for insertion in a lacrimal puncta that is substantially larger or smaller than is typical in most human patients.

Except as where otherwise specified here for use with terminal valves or other mechanism for controlling the dispensing of active-agent containing material, the size of the opening in the lacrimal insert may be from about 1 nm to about 2.5 mm and preferably about 0.15 mm to about 0.8 mm. Instead of one large opening at any one location, multiple small openings may be used. The body of the plug may be wholly or partially transparent or opaque. Optionally, the body may include a tint or pigment that makes the plug easier to see when it is placed in a punctum.

The body of the devices of the present invention may be made of any suitable biocompatible material including silicone, silicone blends, silicone co-polymers, such as, for example, hydrophilic monomers of polyhydroxyethylmethacrylate ("pHEMA"), polyethylene glycol, polyvinylpyrrolidone, and glycerol, and silicone hydrogel polymers such as, for example, those described in U.S. Pat. Nos. 5,962,548, 6,020,445, 6,099,852, 6,367,929, and 6,822,016, incorporated herein in their entireties by reference. Other suitable biocompatible materials include, for example: polyurethane; polymethylmethacrylate; poly(ethylene glycol); poly(ethylene oxide); poly(propylene glycol); poly(vinyl alcohol); poly (hydroxyethyl methacrylate); poly(vinylpyrrolidone) ("PVP"); polyacrylic acid; poly(ethyloxazoline); poly(dimethyl acrylamide); phospholipids, such as, for example, phosphoryl choline derivatives; polysulfobetains; acrylic esters, polysaccharides and carbohydrates, such as, for example, hyaluronic acid, dextran, hydroxyethyl cellulose, hydroxylpropyl cellulose, gellan gum, guar gum, heparan sulfate, chondroitin sulfate, heparin, and alginate; proteins such as, for example, gelatin, collagen, albumin, and ovalbumin; polyamino acids; fluorinated polymers, such as, for example, PTFE, PVDF, and teflon; polypropylene; polyethylene; nylon; and EVA.

The surface of the devices may be wholly or partially coated. The coating may provide one or more of lubriciousness to aid insertion, muco-adhesiveness to improve tissue compatibility, and texture to aid in anchoring the device. Examples of suitable coatings include gelatin, collagen, hydroxyethyl methacrylate, PVP, PEG, heparin, chondroitin sulphate, hyaluronic acid, synthetic and natural proteins, and polysaccharides, thiomers, thiolated derivatives of polyacrylic acid and chitosan, polyacrylic acid, carboxymethyl cellulose and the like and combinations thereof.

Certain embodiments of the devices of the present invention have a body made of a flexible material that conforms to the shape of whatever it contacts. Optionally, in the punctal plug embodiment, there may be a collarette formed of either a less flexible material than that of the body or material that too conforms to the shape of whatever it contacts. When a punctal plug having both a flexible body and a less flexible collarette is inserted into the lacrimal canaliculus, the collarette rests on the exterior of the lacrimal punctum and the body of the punctal plug conforms to the shape of the lacrimal canaliculus. The reservoir and the body of such punctal plugs are preferably coterminous. That is, the reservoir of such punctal plugs preferably make up the entirety of the body, except for the collarette.

In embodiments in which one or both of a flexible body and collarette are used, the flexible body and flexible collarette may be made of materials that include nylon, polyethylene terephthalate ("PET"), polybutylene terephthalate ("PBT"), polyethylene, polyurethane, silicone, PTFE, PVDF, and polyolefins. Punctal plugs made of nylon, PET, PBT, polyethylene, PVDF, or polyolefins are typically manufactured for example and without limitation, extrusion, injection molding, or thermoforming. Punctal plugs made of latex, polyurethane, silicone, or PTFE are typically manufactured using solution-casting processes.

Processes for manufacturing the punctal plugs useful in the present invention are well known. Typically, the devices are manufactured by injection molding, cast molding, transfer molding or the like. Preferably, the reservoir is filled with one or both of at least one active agent and the active agent-containing material subsequent to the manufacture of the device. Additionally, one or more excipients may be combined with the active agent alone or in combination with the polymeric material.

The amount of active agent used in the devices of the present invention will depend upon the active agent or agents selected, the desired doses to be delivered via the device, the desired release rate, and the melting points of the active agent and active agent-containing material. Preferably, the amount used is a therapeutically effective amount meaning an amount effective to achieve the desired treatment, inhibitory, or prevention effect. Typically, amounts of about 0.05 to about 8,000 micrograms of active agents may be used.

In certain aspects of the present invention, the reservoir may be refilled with a material after substantially all of the active agent-containing material has dissolved or degraded and the active agent is released. For example, the new active agent-containing material may be the same as, or different from, the previous polymeric material, and may contain at least one active agent that is the same as, or different from the previous active agent. Certain punctal plugs used for particular applications may preferably be refilled with a material while the punctal plugs remain inserted in the lacrimal canaliculus, while other punctal plugs are typically removed from the lacrimal canaliculus, a new material is added, and the punctal plugs are then reinserted into the lacrimal canaliculus.

After the device is filled with the active agent, the plug is sterilized by any convenient method including ethylene oxide, autoclaving, irradiation, and the like and combination thereof. Preferably, sterilization is carried out through gamma radiation or use of ethylene oxide.

The devices described herein may be used to deliver various active agents for the one or more of the treatment, inhibition, and prevention of numerous diseases and disorders. Each device may be used to deliver at least one active agent and can be used to deliver different types of active agents. For example, the devices can be used to deliver azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The devices may be used to deliver mast cell stabilizers, such as, for example, cromolyn sodium, lodoxamide tromethamine, nedocromil sodium, and permirolast potassium.

The devices may be used to deliver mydriatics and cycloplegics including atropine sulfate, homatropine, scopolamine HBr, cyclopentolate HCl, tropicamide, and phenylephrine HCl. The devices may be used to deliver ophthalmic dyes including rose bengal, sissamine green, indocyanine green, fluorexon, and fluorescein.

The devices may be used to deliver corticosteroids including dexamethasone sodium phosphate, dexamethasone, fluorometholone, fluorometholone acetate, loteprednol etabonate, prednisolone acetate, prednisolone sodium phosphate, medrysone, rimexolone, and fluocinolone acetonide. The devices may be used to deliver non-steroidal anti-inflammatory agents including flurbiprofen sodium, suprofen, diclofenac sodium, ketorolac tromethamine, cyclosporine, rapamycin methotrexate, azathioprine, and bromocriptine.

The devices may be used to deliver anti-infective agents including tobramycin, moxifloxacin, ofloxacin, gatifloxacin, ciprofloxacin, gentamicin, sulfisoxazolone diolamine, sodium sulfacetamide, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine.

The devices may be used to deliver agents for the one or more of the treatment, inhibition, and prevention of glaucoma including epinephrines, including, for example: dipivefrin; alpha-2 adrenergic receptors, including, for example, aproclonidine and brimonidine; betablockers including betaxolol, carteolol, levobunolol, metipranolol, and timolol; direct miotics, including, for example, carbachol and pilocarpine; cholinesterase inhibitors, including physostigmine and echothiophate; carbonic anhydrase inhibitors, including, for example, acetazolamide, brinzolamide, dorzolamide, and methazolamide; prostoglandins and prostamides including latanoprost, bimatoprost, uravoprost, and unoprostone cidofovir.

The devices may be used to deliver antiviral agents, including fomivirsen sodium, foscarnet sodium, ganciclovir sodium, valganciclovir HCl, trifluridine, acyclovir, and famciclovir. The devices may be used to deliver local anesthetics, including tetracaine HCl, proparacaine HCl, proparacaine HCl and fluorescein sodium, benoxinate and fluorescein sodium, and benoxnate and fluorexon disodium. The devices may be used to deliver antifungal agents, including, for example, fluconazole, flucytosine, amphotericin B, itraconazole, and ketocaonazole.

The devices may be used to deliver analgesics including acetaminophen and codeine, acetaminophen and hydrocodone, acetaminophen, ketorolac, ibuprofen, and tramadol. The devices may be used to deliver vasoconstrictors including ephedrine hydrochloride, naphazoline hydrochloride, phenylephrine hydrochloride, tetrahydrozoline hydrochloride, and oxymetazoline. Finally, the devices may be used to deliver vitamins, antioxidants, and nutraceuticals including vitamins A, D, and E, lutein, taurine, glutathione, zeaxanthin, fatty acids and the like.

The active agents delivered by the devices may be formulated to contain excipients including synthetic and natural polymers, including, for example, polyvinylalcohol, polyethyleneglycol, PAA (polyacrylic acid), hydroxymethyl cellulose, glycerine, hypromelos, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids, and sulphobetains.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

The invention claimed is:

1. A lacrimal insert, comprising:
    a body having a first end and a second end;
    a surface extending between the two ends;
    a reservoir contained within the body, wherein the reservoir comprises at least one opening, an active agent-containing material and an active agent;
    a directional release feature connected to the second end; and
    a channel running though the directional release feature from the reservoir to an end of the directional release feature and configured to direct the active agent into lacrimal fluid.

* * * * *